(12) United States Patent
Schneitz et al.

(10) Patent No.: US 6,491,910 B1
(45) Date of Patent: Dec. 10, 2002

(54) OVO ADMINISTRATION OF A COMPETITIVE EXCLUSION CULTURE

(75) Inventors: Carita Elisabeth Schneitz, Helsinki (FI); Esko Viljo Nurmi, Helsinki (FI); Pirjo Marja-Leena Veijalainen, Helsinki (FI)

(73) Assignee: Orion-Yhtyma OY, Espoo (FI)

( * ) Notice: Subject to any disclaimer, the term of this patent is extended or adjusted under 35 U.S.C. 154(b) by 0 days.

(21) Appl. No.: 09/578,153

(22) Filed: May 23, 2000

Related U.S. Application Data

(63) Continuation of application No. 09/033,053, filed on Mar. 2, 1998, now abandoned, which is a continuation of application No. 08/606,713, filed on Feb. 23, 1996, now abandoned.

(30) Foreign Application Priority Data

Mar. 3, 1995 (GB) .............................................. 9504311

(51) Int. Cl.$^7$ ........................ A01N 63/00; A61K 48/00; C12N 1/00; C12N 1/12; D21C 3/00
(52) U.S. Cl. .................... 424/93.3; 424/93.1; 424/93.4; 435/243; 435/252.1
(58) Field of Search ................................ 424/93.1, 93.3, 424/93.4, 93.45, 234.1; 435/243, 252.1

(56) References Cited

U.S. PATENT DOCUMENTS

| | | | | |
|---|---|---|---|---|
| 4,040,388 A | * | 8/1977 | Miller | ........................ 119/1 |
| 4,458,630 A | * | 7/1984 | Sharma et al. | .............. 119/6.8 |
| 4,469,047 A | * | 9/1984 | Miller | ........................ 119/6.8 |
| 4,689,226 A | * | 8/1987 | Nurmi et al. | .............. 424/93.3 |
| 5,206,015 A | * | 4/1993 | Cox et al. | ...................... 424/93 |
| 5,252,309 A | * | 10/1993 | Nuotio et al. | ................. 424/93 |
| 5,451,400 A | * | 9/1995 | Stern et al. | ................. 424/93.3 |
| 5,458,875 A | * | 10/1995 | Casas-Perez et al. | .... 424/93.45 |

FOREIGN PATENT DOCUMENTS

| | | | |
|---|---|---|---|
| EP | 22584 | * | 8/1981 |
| EP | 90909143.1 | * | 6/1990 |
| EP | 0 479 820 B1 | * | 4/1992 |
| WO | 90/14765 | * | 12/1990 |
| WO | 91/00099 | * | 1/1991 |
| WO | 92/12638 | * | 8/1992 |
| WO | 94/03195 | * | 2/1994 |
| WO | 94/21127 | * | 9/1994 |

OTHER PUBLICATIONS

Timoney et al., Hagan and Bruner's microbiology and infectious diseases of domestic animals, 1988, Cornell University Press, Ithaca, NY, pp. 223–224.*

Schneitz et al., Droplet application for protecting chicks against salmonella colonisation by competitive exclusion, 1990, the Veterinary Record, p. 510.*

Timoney, J.F., Hagan and Bruner's Microbiology and Infections Discases of Domestic Animals, Eighth Ed., Cornell University Press Ithica, New York 1988.*

Cox et al., "Research Note: In Ova Administration of a Competitive Exclusion Culture Treatment to Broiler Embryos," *Poultry Science* 71:1781–1784 (1992).*

Schneitz et al., "Droplet application for protecting chicks against salmonella colonization by competitive exclusion," *The Veterinary Record* 126 (20) 510 (1990).*

* cited by examiner

*Primary Examiner*—Remy Yucel
*Assistant Examiner*—Sumesh Kaushal
(74) *Attorney, Agent, or Firm*—Finnegan, Henderson, Farabow, Garrett & Dunner, L.L.P.

(57) ABSTRACT

An improved method of competitively excluding pathogens capable of intestinal colonization, such as Salmonella or Cambylobacter, from a digestive tract of a bird comprises administration in ovo to a fertile bird egg of a competitive exclusion (CE) culture essentially free from bacteria which abundantly form gas such as Clostridium species. The CE culture may be any CE culture essentially free from abundant gas forming bacteria which culture is derived from a digestive tract of a bird free from pathogens. The CE culture may be administered either into the air cell or the amnion of a fertile bird egg, preferably into the amnion.

16 Claims, No Drawings

OVO ADMINISTRATION OF A COMPETITIVE EXCLUSION CULTURE

This is a continuation of a U.S. application Ser. No. 09/033,053, filed Mar. 2, 1998 now abandoned, which is a continuation of a U.S. application Ser. No. 08/606,713, filed Feb. 23, 1996 now abandoned, which claims priority to a foreign Application No. U.K. 9504311.3 filed Mar. 3, 1995

The present invention relates to a method of competitively excluding pathogens capable of intestinal colonization, especially Salmonella, from the digestive tract of a bird, comprising administration of a competitive exclusion (CE) culture essentially free from abundant gas forming bacteria in ovo to a fertile bird egg.

Poultry is the most important source of human gastrointestinal infections, such as Salmonella and Cambylobacter infections. For a long time *Salmonella infantis* has been a very common Salmonella type that cause human Salmonella infections. Now there has also been an alarming increase in the incidence of human food poisoning associated with *Salmonella enteritis* PT4. See L. Nuotio, C. Schneitz, U. Halonen and E. Nurmi, *British Poultry Science* 33, 775–779 (1992). Much of the increase has been associated with eating raw or undercooked eggs that were contaminated with salmonellas, but broilers are also a considerable reservoir of infection for man, even in relation to handling of newly-hatched chicks. Broiler chicks can be infected through transovarian transmission and the salmonellas may also spread via contaminated feed. There are several reports in which the epidemically implicated or suspected vehicle of cambylobacteriosis has been raw, barbecued or undercooked chicken. In addition to human infections the broilers themselves may be infected by pathogens causing mortality, such as some Clostridium species.

Competitive exclusion is a method of preventing pathogenic bacteria from colonizing birds and thus infecting man and birds themselves. Because of the diverse sources of contamination it is difficult to administer a competitive exclusion culture to a bird before it is colonized by pathogenic bacteria. N. A. Cox et al., *Poultry Science* 71, 1781–1784 (1992), describes a study of in ovo administration of a competitive exclusion culture treatment to broiler embryos. U.S. Pat. No. 5,206,015 discloses a method and apparatus for introducing probiotic bacteria into the digestive tract of a bird in order to exclude undesirable bacteria therefrom, and inoculated eggs produced thereby. In a preferred embodiment of the invention, a fertile bird egg is administered a Salmonella competitive exclusion culture, such as disclosed in U.S. Pat. No. 4,689,226 and U.S. Pat. No. 4,335,107. The culture may optionally include an oxygen scavenging agent such as cysteine as described in U.S. Pat. No. 4,657,762. The culture preferably comprises at least one anaerobic bacteria of intestinal origin.

According to U.S. Pat. No. 5,206,015 the culture is preferably administered into the amnion or the air cell of the egg. Most preferably the bacterial culture is deposited in the air cell. However the amnion of the egg for the bacterial deposition seems to be a problem. In fact, according to the description, putting the CE culture into the amnion killed most of the chicks before hatch, even at 1:1,000,000 dilution.

The above mentioned patent discloses also the problem that when an undiluted CE culture was placed in the air cell, hatchability was significantly reduced when compared to controls.

The object of the present invention is to provide a better and more advantageous method compared to prior art for competitively excluding pathogens capable of intestinal colonization, from the digestive tract of a bird. The pathogens capable of intestinal colonization are e.g. Salmonella sp., Cambylobacter sp. and *Escherichia Coli*.

Specifically the present invention provides an advantageous method for competively excluding Salmonella from the digestive tract of a bird prior to colonization by Salmonella.

Competitive exclusion essentially comprises the prevention of the population of the gut by pathogens through pre-populating the gut with non-pathogenic microflora. Typically the bacteria strains in a CE culture produced by the method described in U.S. Pat. No. 5,206,015 include spore-forming bacteria, such as different Clostridium species, (see H. Pivnick, B. Blanchfield and J. Y. D'Aoust, *Journal of Food Protection* 44, 909 (1981) and H. Pivnick and E. Nurmi, *Developments in Food Microbiology* 1, 41 (1982)), which are known to form abundantly gas.

It has unexpectedly been found that the hatchability is significantly increased when CE cultures, which are essentially free from abundant gas forming bacteria, are administered in ovo to a fertile bird egg, either to the region of the air cell or the amnion, compared with that described in U.S. Pat. No. 5,206,015. Especially the difference between the hatchabilities of the eggs where the CE cultures are administered into the amnion is drastic showing that CE cultures which are essentially free from abundant gas forming bacteria can be administered to the amnion without killing the embryo.

Administration of the CE culture preparations to the amnion is more beneficial compared to the air cell, because the bird comes in contact with the protective bacteria in the earliest possible stage. Also the anaerobic bacteria in a CE culture preparation are more viable in the amnion than in the air cell. Thus the problem with e.g. Salmonella infected breeders and Salmonella contaminated egg shells will be minimized.

Moreover it has been found that CE cultures may be coadministered in ovo with commonly used vaccines, such as Marek's vaccine, in the poultry industry. The vaccines are usually administered to the amnion, which makes the region of amnion more preferable administration site than the air cell.

The invention provides an improved method for competitively excluding pathogens capable of intestinal colonization, such as Salmonella or Cambylobacter, comprising administration in ovo to a fertile bird egg of a CE culture essentially free from bacteria which abundantly form gas. The CE culture may be any CE culture essentially free from abundant gas forming bacteria derived from digestive tract of mature birds which are free from pathogens, such as Salmonella. It may be undiluted or diluted. Preferably the CE culture is prepared as described in U.S. Pat. No. 4,689,226 or EP-A-479 820 which are checked to be essentially free from abundant gas formers,such as Clostridia.

U.S. Pat. No. 4,689,226 describes a bacterial preparation for the prophylaxis of intestinal disturbances in poultry caused by pathogenic bacteria. The preparation is made by anaerobically cultivating either separately or together bacteria strains of normal alimentary tract bacterial species having an adhesion efficiency onto the epithelial cells of the alimentary tract of poultry of at least 10 bacteria per epithelial cell, and isolating the cultivated bacteria. The bacterial strains are cultivated preferably together with epithelial cells from the alimentary tract, for example from the crop of the chicken. After the cultivation, the bacteria are isolated from the culture broth and finished to a preparation, for instance by lyophilization. The test for adhesion may be carried out by a known method, for instance according to the Fuller adhesion test.

According to U.S. Pat. No. 4,689,226 the isolation of suitable bacteria strains can be performed as follows:

The content of the alimentary tract of an adult chicken is mechanically removed. After this, loose and weakly attached bacteria are removed, for instance by washing with a phosphate buffered saline. The washed alimentary tract, or part of it, preferably the crop or the caecum with the attached bacteria remaining, is minced, suitably diluted and cultured to obtain pure cultures. Bacterial strains with good adhering ability are selected for the cultivation of the final preparation. Especially good results are obtained when two or more bacterial strains are cultivated together.

EP-A-479820 describes a bacterial preparation useful for the prophylaxis of colonization of human pathogenic bacteria, especially Cambylobacter species, in poultry comprising bacteria derived from an adult bird, from the microecological niche which pathogenic bacteria occupy. The bacterial flora of the preparation is derived from the caecal mucous layer of adult birds. Highly effective floras are those which are obtained by culturing the bacterial flora from the mucous layer of the caecal wall from an adult bird under either anaerobic or microaerophilic conditions, preferably in a mucin broth.

The culture may optionally include an oxygen scavenging agent such as cysteine as described in U.S. Pat. No. 4,657,762. Most preferably the CE culture is prepared as described in U.S. Pat. No. 4,689,226. One of the most preferable CE cultures is commercially available from Orion Corporation marketed under the trademark BROILACT®, which is cultured from biological material deposited under the name "Production inoculum SHGO1B" and under ATCC accession number 55715. The biological material was deposited on Oct. 3, 1995, with the American Type Culture Collection, Va. 20110-2209 U.S.A.

The CE culture is administered either into the air cell or the amnion of a fertile bird egg close to hatch, for example, when at least 60%, preferably 70%, more preferably 75% of the incubation time has elapsed. The CE culture is administered in an amount effective to colonize the digestive tract of the embryonic bird. Preferably the CE culture is administered into the amnion including the amniotic fluid, the yolk sac and the embryo itself. A suitable dose for BROILACT® is from about 0.01 mg to 1 mg per egg, preferably about 0.1 mg per egg when administered into the amnion. After injection the eggs are incubated to hatch. The digestive tracts of the hatchlings of these eggs are colonized by the CE culture at the time of hatch.

The present invention may be practiced with any type of bird egg, including chicken, turkey, duck, goose, quail or pheasant eggs. Preferred eggs are chicken and turkey eggs. Most preferred eggs are chicken eggs.

Chicken eggs are injected on about the fifteenth to nineteenth day of incubation, preferably on the nineteenth day of incubation.

The injection of a bird egg may be done manually, but an automated injection is preferred. A suitable apparatus is described in U.S. Pat. No. 5,206,015.

EXAMPLE 1

Preparing the Competitive Exclusion (CE) Culture

The CE culture was a mixed culture which did not contain clostridia. The culture originated from an adult hen and was derived as described in U.S. Pat. No. 4,689,226. The caecum of an adult hen was removed, aseptically opened and mechanically cleaned. After this the caecum was washed several times with sterile phosphate buffered saline and the epithelial cells were scraped off and propagated anaerobically in a TSB-CAP medium at 41° C. for 24 hours. The composition of the TSB-CAP medium was as follows:

| | |
|---|---|
| Trypticase Soy Broth (BBL 11768) | 30.0 g |
| L-cysteine (Merck 2829) | 0.4 g |
| Agar (Merck 1614) | 0.6 g |
| $K_2HPO_4$ (Merck 5101) | 2.1 g |
| $KH_2PO_4$ (merck 4873) | 1.1 g |
| Clean water | ad. 1000 ml |
| pH +/− 7.3 | |

Administration of CE Culture in ovo

20 Ross 1 broiler eggs on day 19 of incubation from a commercial hatchery without any cracks were chosen for this study The eggs were placed in an egg tray with the blunt end up, which was cleaned with alcohol. A small hole, big enough for a 21 gauge needle, was pierced manually. Eggs in group I were injected with 0.2 ml of undiluted CE culture into one-half of an inch through the blunt end of the egg i.e. into the air cell. Eggs in group II were injected with the same amount of undiluted CE culture one inch deep through the blunt end of the egg i.e. into the amnion. After injection the hole in the egg shell was covered with melted paraffin and the eggs were placed in a normal laboratory incubator at 37° C. to be hatched. Eight birds hatched in a laboratory hatcher were chosen to the control group.

The hatchability results are presented in Table 1. The rate of hatchability was high although the CE culture used was undiluted and the fertility of the eggs was not controlled before the administration of the CE culture. The results also indicate that it is possible to administer a CE culture in ovo to the amnion without killing the embryo.

Efficacy Testing

One day after hatch the chicks were taken to the rearing facilities and they were challenged individually with tubing and syringe straight into the crop with $10^3$ cfu (colony froming units) of a nalidixic acid resistant derivative of *Salmonella infantis* per bird.

Five days after challenge the chicks were asphyxiated with $CO_2$ and their caeca were examined for Salmonella. The results are given in Table 1. The untreated control chicks were readily colonized whereas the CE treated chicks harboured only low numbers of Salmonella in their caeca.

TABLE 1

| Group | Site of injection | Hatched | IF[1] | PF[2] |
|---|---|---|---|---|
| I | air cell | 9/10 | 1.2 | 5.5 |
| II | amnion | 6/10 | 1.3 | 5.1 |
| Control | — | — | 6.6 | — |

[1]The IF is the geometric mean of the number of salmonellas per gram for all chicks in a particular group.
[2]The protection factor (PF) is the IF of the control group divided by the IF of the treatment group.

EXAMPLE 2

Preparation of the BROILACT® Suspensions

The dose volume for in ovo administration was 0.05 ml. 1 g of lyophilized BROILACT® was suspended aseptically into 50 ml of sterile cysteine buffer in order to obtain a concentration of 1 mg/0.05 ml. A tenfold dilution of this suspension was made to cysteine buffer in order to obtain a concentration of 0.1 mg/0.05 ml (10 ml of the suspension into 90 ml of cysteine buffer).

The cysteine buffer was as follows:

| | |
|---|---|
| L-cysteine | 1.25 g |
| $KH_2PO_4$ | 1.36 g |
| $K_2HPO_4$ | 2.63 g |
| clean water | 500 ml |
| autoclave at 121° C. for 15 minutes. | |

Administration of BROILACT® in Ovo

Eight trays with 144 Ross/32 eggs on each tray, altogether 1152 eggs, were candled in order to obtain 8×100 eggs containing live embryos. Eggs were maintained under warm room conditions during candling and transfer (75–85° F.). Altogether 213 eggs were pulled out of setter at day 19 of incubation and injected in ovo manually into the air cell or the amnion by needle and syringe. After injection the eggs were placed in a hatcher, the BROILACT® treated chicks and the control chicks in separate hatchers.

The eggs were divided in to fourteen groups: altogether 30 eggs in groups I and II 33 eggs in groups IIII and IV, V and VI, VII and VII, 28 eggs in groups IX and X, 30 eggs in groups XI and XII and 26 eggs in groups XII and XIV. The blunt end of each egg was sprayed with 0.5% chlorine bleach solution (10 ml bleach per 90 ml water) prior to punching the hole. All eggs in groups l–XII were manually punched with an 18 gauge needle adapted with a rubber stopper to allow penetration only to 2 mm, prior to injection.

The eggs in groups I and II were injected with 1 mg per egg of BROILACT® and III and IV with 0.1 mg into the air cell (one-half of an inch through the blunt end) and eggs in groups V and VI and VII and VII with same doses of BROILACT® into the amnion (one inch through the blunt end of an egg), respectively. The dose volume of BROILACT® was 0.05 ml. Eggs in groups IX and X were injected with cysteine buffet into the air cell and in groups XI and XII were injected with cysteine buffer into the amnion. The dose volume of cysteine was 0.05 ml. Eggs in groups XII and XIV remained untreated.

The hatchability results are presented in Table 2. The results show that the hatchability of the air cell treated eggs was not significantly reduced when compared to controls. The hatchability of the amnion treated groups was dependent on the BROILACT® dosage: the dose 0.1 mg gave commercially acceptable hatchability.

Efficacy Testing

One day after hatch the chicks were taken to the rearing facilities and the chicks in groups I–VIII were challenged individually with tubing and syringe straight into the crop with $10^3$ cfu of nalidixic acid resistant derivative of *Salmonella infantis* per bird. Six days after the challenge, 9th day of life, all the birds were asphyxiated with $CO_2$ and their caeca were examined both quantitatively and qualitatively for Salmonella.

The resistance of the hatched chicks to *Salmonella infantis* challenge is presented in Table 2. All the chicks treated with BROILACT® were more resistant to Salmonella than the chicks in the cysteine buffer treated control groups.

TABLE 2

| Group | In ovo treatment | $N^A$ | $IF^B$ | Hatched % alive (% dead) | Hatched No. alive/all (No. dead) |
|---|---|---|---|---|---|
| I, II | BROILACT® 1.0 mg, air cell | 18 | 3.2 | 90 | 27/30 |
| III, IV | BROILACT® 0.1 mg, air cell | 20 | 3.8 | 94 (3) | 31/33 (1) |
| V, VI | BROILACT® 1.0 mg, amnion | 13 | 0.8 | 48 (10) | 16/33 (3) |
| VII, VIII | BROILACT® 0.1 mg, amnion | 16 | 1.1 | 79 (6) | 26/33 (2) |
| IX, X | cyst. buffer, air cell | 20 | 5.6 | 100 | 28/28 |
| XI, XII | cyst. buffer, amnion | 19 | 6.0 | 97 | 29/30 |
| XIII, XIV | 0-control | 20 | $ND^D$ | 100 | 26/26 |

$^A$Total number of chicks in two groups
$^B$The result for an individual chick is presented as Infection Factor (IF) which is the logarithmic number of salmonellas per gram of caecal contents. If salmonella is only found by enrichment the IF value is considered 1. The IF value presents the mean value of the chicks rared in the two separate groups.
$^C$dose volume of BROILACT® and cysteine buffer was 0.05 ml
$^D$no salmonellas were detected in the 0-control groups

EXAMPLE 3

Preparation of the BROILACT® Suspensions

The suspension of concentration 0.1 mg/0.05 ml was made from lyophilized BROILACT® as described in example 2. A tenfold dilution of this suspension was made to cysteine buffer in order to obtain a concentration of 0.01 mg/0.05 ml. The dose volume for in ovo administration was 0.05 ml.

Administration of BROILACT® V in Ovo and Efficacy Testing

150 Ross eggs containing live embryos were divided into three different treatment groups: I and II, IIII and IV, and V and VI. Altogether 50 eggs were in each treatment group. The in ovo administration procedure was the same as described in example 2 except that all the injections were made into the amnion. The eggs in groups I and II were injected with 0.05 ml of cysteine buffer. The eggs in groups IIII and IV were injected with 0.05 ml of the suspension of concentration 0.1 mg/0.05 ml and eggs in groups V and VI were injected with the suspension of concentration 0.01 mg/0.05 ml. The hatchability results are presented in Table 3.

The efficacy was tested by the procedure described in example 2. The resistance of the hatched chicks to *Salmonella infantis* challenge is presented in Table 3. All the chicks treated with BROILACT® were more resistant to Salmonella than the chicks in the cysteine buffer treated control groups.

TABLE 3

| Group | In ovo treatment | $IF^A$ | Hatched % alive (% dead) | Hatched No. alive/all (No. dead) |
|---|---|---|---|---|
| I, II | cysteine buffer 0.05 ml | 6.9 | 98 (2) | 49/50 (1) |

TABLE 3-continued

| Group | In ovo treatment | IF[A] | Hatched % alive (% dead) | Hatched No. alive/all (No. dead) |
|---|---|---|---|---|
| III, IV | BROILACT® 0.1 mg | 2.0 | 90 (10) | 45/50 (5) |
| V, VI | BROILACT® 0.01 mg | 3.4 | 98 (2) | 49/50 (1) |

[A]The result for an individual chick is presented as Infection Factor (IF) which is the logarithmic number of salmonellas per gram of caecal contents. If salmonella is only found by enrichment the IF value is considered 1. The IF value presents the mean value of the two separate groups.

What is claimed is:

1. A method of competitively excluding from the digestive tract of birds pathogens that colonize the intestines, comprising administering in ovo to fertile bird eggs a mixed competitive exclusion culture free from bacteria which abundantly form gas.

2. A method as claimed in claim 1, which comprises competitively excluding Salmonella pathogens.

3. A method as claimed in claim 1, which comprises competitively excluding the Campylobacter pathogens.

4. A method as claimed in claim 1, which comprises competitively excluding Eschenchea coli pathogen.

5. A method as claimed in claim 1, wherein the mixed competitive exclusion culture is obtained from ATCC accession number 55715.

6. A method as claimed in claim 1, wherein the eggs are subjected to an incubation period to hatch, and wherein the mixed competitive exclusion culture is administered when at least 60% of the incubation period has elapsed.

7. A method as claimed in claim 6, wherein at least 70% of the incubation period has elapsed.

8. A method as claimed in claim 6, wherein at least 75% of the incubation period has elapsed.

9. A method as claimed in claim 1, wherein the mixed competitive exclusion culture is co-administered with a vaccine.

10. A method as claimed in claim 1, wherein the bird eggs are chicken eggs.

11. A method as claimed in claim 1, wherein the bird eggs are turkey eggs.

12. A method as claimed in claim 1, which comprises administering the mixed competitive exclusion culture to the air cell of the bird eggs.

13. A method as claimed in claim 12, wherein the hatchability of the eggs is at least 90%.

14. A method as claimed in claim 1, which comprises administering the mixed competitive exclusion culture to the amnion of the bird eggs.

15. A method as claimed in claim 14, wherein the hatchability of the eggs is at least 79%.

16. A method of competitively excluding from the digestive tract of birds pathogens that colonize the intestines, comprising administering in ovo to fertile bird eggs a mixed competitive exclusion culture free from Clostridia.

* * * * *

UNITED STATES PATENT AND TRADEMARK OFFICE
CERTIFICATE OF CORRECTION

PATENT NO. : 6,491,910 B1
DATED : December 10, 2002
INVENTOR(S) : Schneitz et al.

It is certified that error appears in the above-identified patent and that said Letters Patent is hereby corrected as shown below:

<u>Title page, Item [54] and Column 1, lines 1 and 2,</u>
Title, "OVO ADMINISTRATION OF A COMPETITIVE EXCLUSION CULTURE" should read -- IN OVO ADMINISTRATION OF A COMPETITIVE EXCLUSION CULTURE --.

<u>Column 7,</u>
Line 23, after "exclusing", delete "the".
Line 25, "*Eschenchea coli*" should read -- *Escherichia coli* --.

Signed and Sealed this

Twenty-ninth Day of April, 2003

JAMES E. ROGAN
*Director of the United States Patent and Trademark Office*